United States Patent
Nishimura et al.

(10) Patent No.: US 9,186,204 B2
(45) Date of Patent: Nov. 17, 2015

(54) ENDOSCOPIC HIGH-FREQUENCY HEMOSTATIC FORCEPS

(75) Inventors: Makoto Nishimura, Nagano (JP); Miyuki Nishimura, Nagano (JP)

(73) Assignees: RIVER SEIKO CORPORATION, Okaya-shi (JP); KANEKA CORPORATION, Osaka (JP)

( * ) Notice: Subject to any disclaimer, the term of this patent is extended or adjusted under 35 U.S.C. 154(b) by 815 days.

(21) Appl. No.: 13/265,608

(22) PCT Filed: Nov. 13, 2009

(86) PCT No.: PCT/JP2009/006070
§ 371 (c)(1),
(2), (4) Date: Jan. 4, 2012

(87) PCT Pub. No.: WO2010/131309
PCT Pub. Date: Nov. 18, 2010

(65) Prior Publication Data
US 2012/0101501 A1    Apr. 26, 2012

(30) Foreign Application Priority Data
May 13, 2009 (JP) .................. 2009-116192

(51) Int. Cl.
*A61B 18/14* (2006.01)
*A61B 18/00* (2006.01)
*A61B 17/29* (2006.01)

(52) U.S. Cl.
CPC ......... *A61B 18/1445* (2013.01); *A61B 18/1442* (2013.01); *A61B 17/29* (2013.01); *A61B 2018/00083* (2013.01); *A61B 2018/00589* (2013.01); *A61B 2018/00595* (2013.01)

(58) Field of Classification Search
CPC .. A61B 17/29; A61B 18/085; A61B 18/1442; A61B 18/1445

USPC ....................................... 606/51, 52
See application file for complete search history.

(56) References Cited

U.S. PATENT DOCUMENTS 5,217,460 A * 6/1993 Knoepfler ................. 606/52
5,263,967 A * 11/1993 Lyons et al. .............. 606/205

(Continued)

FOREIGN PATENT DOCUMENTS

JP    11-019086 A    1/1999
JP    2000-102545 A    4/2000

(Continued)

OTHER PUBLICATIONS

Extended European Search Report dated Oct. 2, 2012, issued in corresponding European patent application No. 09844583.6.

(Continued)

*Primary Examiner* — Christopher A Flory
(74) *Attorney, Agent, or Firm* — Westerman, Hattori, Daniels & Adrian, LLP

(57) ABSTRACT

A hemostatic forceps (20) includes a pair of forceps elements (forceps cups (1)) constituted of a conductive metal and configured to serve as high-frequency electrodes and configured to be able to change into a state where front portions of the pair of forceps cups (1) are open, and a state where the pair of forceps cups (1) are close. A sawtooth portion (15) having a plurality of concavo-convex structures which constitute a sawtooth-shape is provided on at least one of respective closing-side surfaces (17) of the pair of forceps cups (1). The sawtooth portion (15) is provided with an electrically insulative coating over its bottom portion (21), but not on a top portion (22) thereof, and hence the top portion (22) is conductive.

6 Claims, 10 Drawing Sheets

(56) References Cited

U.S. PATENT DOCUMENTS

| | | | |
|---|---|---|---|
| 5,275,615 A | 1/1994 | Rose | |
| 5,674,220 A * | 10/1997 | Fox et al. | 606/51 |
| 5,891,142 A | 4/1999 | Eggers et al. | |
| 6,887,240 B1 * | 5/2005 | Lands et al. | 606/51 |
| 6,969,389 B2 * | 11/2005 | Kidooka | 606/51 |
| 7,887,535 B2 * | 2/2011 | Lands et al. | 606/51 |
| 8,579,897 B2 * | 11/2013 | Vakharia et al. | 606/52 |
| 2001/0037109 A1 | 11/2001 | Yamauchi et al. | |
| 2003/0144652 A1 | 7/2003 | Baker et al. | |
| 2004/0199160 A1 * | 10/2004 | Slater | 606/48 |
| 2005/0075631 A1 * | 4/2005 | Kidooka | 606/51 |
| 2005/0187547 A1 | 8/2005 | Sugi | |
| 2006/0173452 A1 * | 8/2006 | Buysse et al. | 606/50 |
| 2007/0149971 A1 * | 6/2007 | Nishimura | 606/51 |
| 2008/0294159 A1 | 11/2008 | Akahoshi et al. | |
| 2010/0057085 A1 * | 3/2010 | Holcomb et al. | 606/51 |

FOREIGN PATENT DOCUMENTS

| | | |
|---|---|---|
| JP | 2002-078717 A | 3/2002 |
| JP | 2004-229976 A | 8/2004 |
| JP | 2008-000582 A | 1/2008 |
| JP | 2009-006128 A | 1/2009 |
| WO | 94/17741 A1 | 8/1994 |

OTHER PUBLICATIONS

International Search Report of PCT/JP2009/006070, mailing date Dec. 15, 2009.

* cited by examiner

ENDOSCOPIC HIGH-FREQUENCY HEMOSTATIC FORCEPS

TECHNICAL FIELD

The present invention relates to an endoscopic high-frequency hemostatic forceps applicable to hemostasis of a biological tissue.

BACKGROUND ART

An endoscopic hemostatic forceps is utilized to apply a high-frequency current to a pair of high-frequency electrodes pinching a biological tissue therebetween to thereby coagulate the biological tissue by cauterization. In the case where the high-frequency electrodes contacting the biological tissue have a large area, it takes a long time before the contact portion is sufficiently heated for attaining a hemostatic effect. In this case, the biological tissue suffers a deep burn therein over an extensive area thus suffering unnecessary tissue destruction, while the hemostatic effect, which is the object of the treatment, cannot be attained as desired. Accordingly, a forceps type high-frequency treatment instrument has been proposed that includes a pair of forceps cups constituted of a conductive metal that serves as high-frequency electrodes and configured to be able to change into a state where front portions of the pair of forceps cups are open, and a state where the pair of forceps cups are close, the forceps cups being provided with an electrically insulative coating over an entirety thereof, except for an outer periphery of the closing-side surface of the respective forceps where the conductive metal is exposed (see, for example, patent document 1).

RELATED DOCUMENT

Patent Document

[Patented Document 1] Japanese Laid-Open Patent Publication No. H11-19086

DISCLOSURE OF THE INVENTION

Employing the high-frequency treatment instrument that includes the pair of forceps cups serving as high-frequency electrodes according to the patented document 1 allows the area of the high-frequency electrode brought into contact with the biological tissue to be substantially reduced, and the biological tissue pinched by the pair of forceps cups to be securely fixed therebetween. Accordingly, the high-frequency cauterization can be performed as desired on a target part. However, in the forceps type high-frequency treatment instrument according to the patented document 1, the entire outer periphery of the closing-side surface of the forceps cups, which contacts the biological tissue, constitutes an exposed metal surface. Here, the temperature of a biological tissue increases in proportion to a square of the current density of the high-frequency current, and therefore the biological tissue is not heated such that the hemostatic effect is instantaneously attained. This is because the high-frequency treatment instrument according to the patented document 1 is not intended for hemostasis but for collecting a tissue by resection from an organism. Accordingly, employing the forceps type high-frequency treatment instrument according to the patented document 1 for a hemostatic treatment may cause a deep burn as schematically illustrated in FIG. 11, in the biological tissue contacted by an exposed metal portion 100a of a forceps cup 100 thereby incurring unnecessary tissue destruction, which may result in bleeding or perforation several days later.

The present invention has been accomplished in view of the foregoing problem, with an object to provide an endoscopic high-frequency hemostatic forceps that allows a hemostatic treatment by a high-frequency current to be safely and quickly performed without causing a deep burn in the biological tissue.

Accordingly, the present invention provides an endoscopic high-frequency hemostatic forceps including a pair of forceps elements constituted of a conductive metal so as to serve as a high-frequency electrode, and configured to be able to freely change into a state where front portions of the pair of forceps elements are open, or a state where the pair of forceps elements are close, comprising a sawtooth portion having a plurality of concavo-convex structures which constitute a sawtooth-shape formed on at least one of the respective opposing closing-side surfaces of the pair of forceps elements, wherein a bottom portion of the sawtooth-shape of the sawtooth portion is provided with an electrically insulative coating, and a top portion of the sawtooth-shape of the sawtooth portion is not provided with the electrically insulative coating but conductive.

The top portion of the sawtooth-shape of the sawtooth portion may be formed in a planar shape, and the sawtooth portion may be provided with the electrically insulative coating except for the top portion.

Also, a front edge portion of the closing-side surface may be formed without the sawtooth portion. The front edge portion of the closing-side surface may be either conductive without the electrically insulative coating, or provided with the electrically insulative coating.

Alternatively, the sawtooth portion may be formed on the front edge portion of the closing-side surface.

The pair of forceps elements may each include the sawtooth portion formed on the respective closing-side surfaces, such that top portions of the respective sawtooth portions of the pair of forceps elements confront each other when the pair of forceps elements are closed. Alternatively, the pair of forceps elements may each include the sawtooth portion formed on the respective closing-side surfaces, such that the respective sawtooth portions of the pair of forceps elements are engaged with each other when the pair of forceps elements are closed.

Further, the pair of forceps elements may each include an opening formed on the respective closing-side surfaces, and an inner surface of the opening may be conductive without the electrically insulative coating.

The pair of forceps elements may each include the sawtooth portion formed on the respective closing-side surfaces, and the pair of forceps elements electrically connected to each other and serves as a monopolar high-frequency electrode. With such a configuration, the hemostatic treatment can be as safely performed as in the case of employing a bipolar high-frequency electrode.

Thus, the endoscopic high-frequency hemostatic forceps according to the present invention includes the sawtooth portion having a plurality of concavo-convex structures which constitute a sawtooth-shape formed on the closing-side surface of the forceps element, and the bottom portion of the sawtooth-shape of the sawtooth portion is provided with the electrically insulative coating while the top portion of the sawtooth-shape of the sawtooth portion is made conductive. Such a configuration allows a biological tissue brought into contact with the top portion to be instantaneously cauterized at a high temperature, thereby enabling a high-frequency hemostatic treatment to be safely and quickly performed without causing a deep burn in the biological tissue.

BRIEF DESCRIPTION OF THE DRAWINGS

The above and other objects, features and advantages of the present invention will become more apparent through the following embodiments described referring to the accompanying drawings.

DESCRIPTION OF EMBODIMENTS

Figure 1:
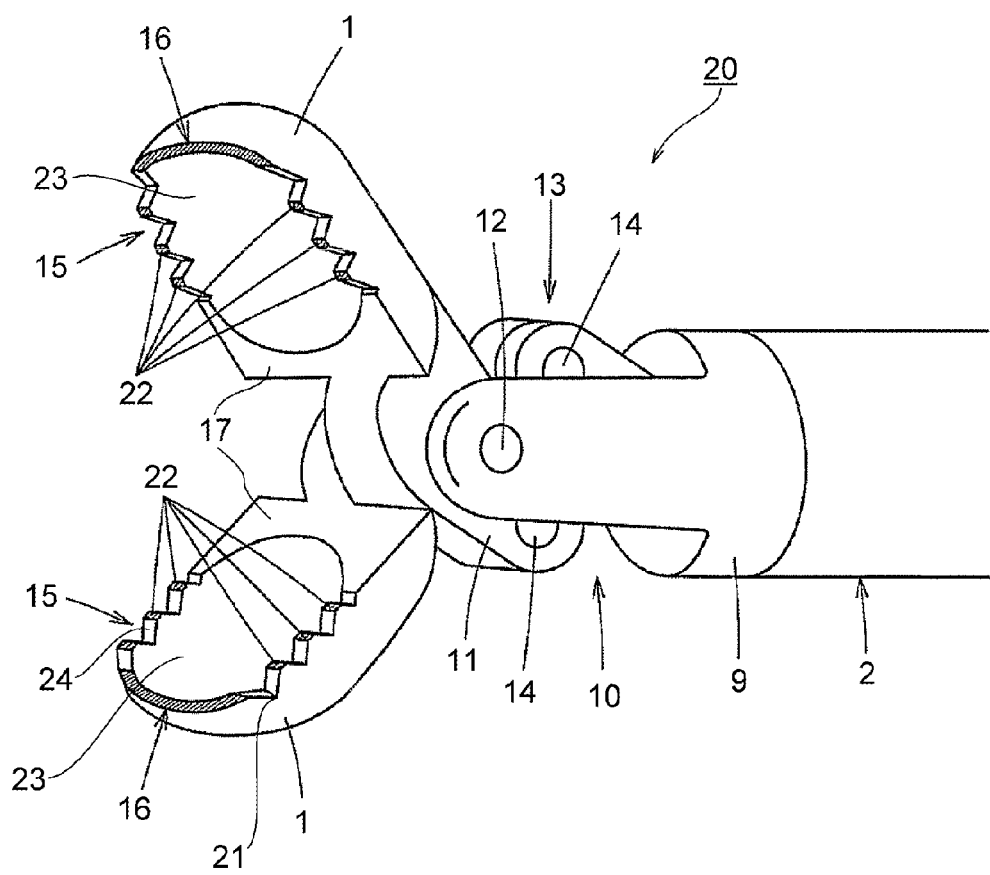
FIG. 1 is a perspective view showing a distal portion of an endoscopic high-frequency hemostatic forceps according to a first embodiment of the present invention.

Hereafter, embodiments of the present invention will be described in details referring to the drawings.

FIG. 1 is a perspective view showing a distal portion of an endoscopic high-frequency hemostatic forceps (hemostatic forceps 20) according to a first embodiment of the present invention.

First, a general description of the hemostatic forceps 20 according to this embodiment will be given.

The hemostatic forceps 20 includes a pair of forceps elements (forceps cups 1) constituted of a conductive metal so as to serve as a high-frequency electrode, and configured to be able to freely change into a state where front portions of the pair of forceps elements are open, and a state where the pair of forceps elements are close.

A sawtooth portion 15 having a plurality of concavo-convex structures which constitute a sawtooth-shape is provided on at least one of opposing closing-side surfaces 17 of the pair of forceps cups 1. A bottom portion 21 of the sawtooth-shape of the sawtooth portion 15 is provided with an electrically insulative coating, while a top portion 22 of the sawtooth-shape of the sawtooth portion 15 is not provided with the electrically insulative coating but conductive.

The hemostatic forceps 20 according to this embodiment will now be described in further details.

Figure 2:
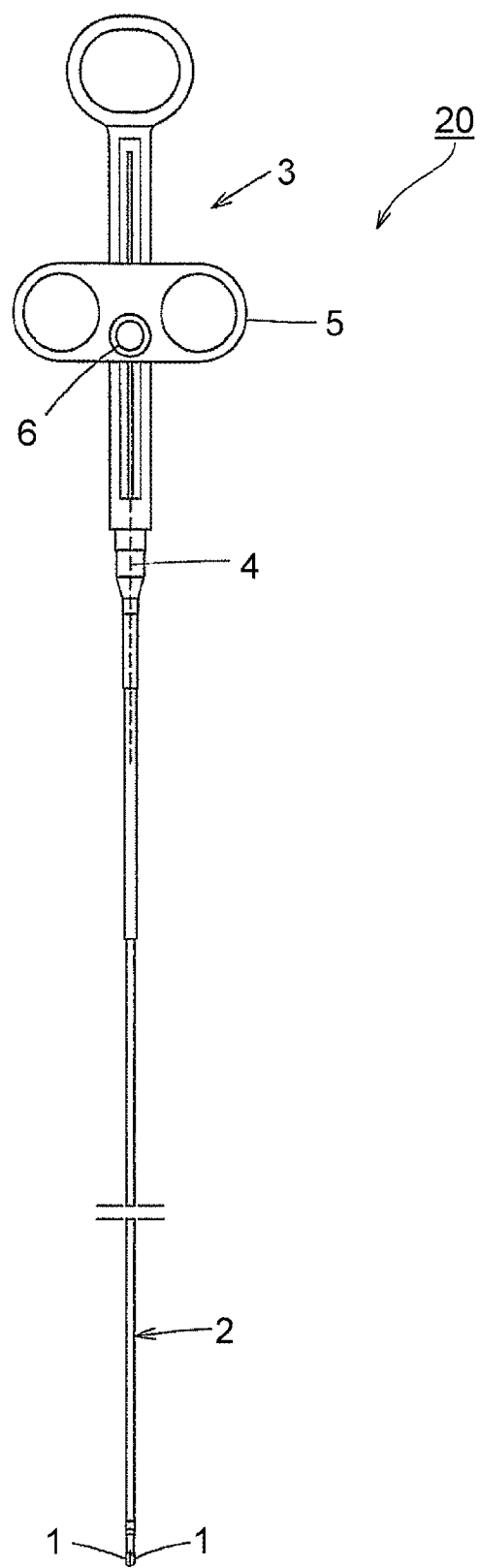
FIG. 2 is a drawing showing an overall configuration of the endoscopic high-frequency hemostatic forceps according to the first embodiment of the present invention.

FIG. 2 is a drawing showing an overall configuration of the hemostatic forceps 20 according to this embodiment. The pair of forceps cups 1 serving as a high-frequency electrode is provided at a distal portion of a flexible sheath 2. A conductive operating wire 4 is provided through the flexible sheath 2, and a slider 5 used to slide the operating wire 4 in a longitudinal direction is provided in a manipulating portion 3 connected to a proximal portion (base portion). Upon connecting a high-frequency power supply cable (not shown) to a monopolar connector 6 provided to the slider 5, a high-frequency current can be supplied to the forceps cup 1 through the operating wire 4. Thus, the hemostatic forceps 20 according to this embodiment is what is known as a monopolar high-frequency treatment instrument.

Figure 3:
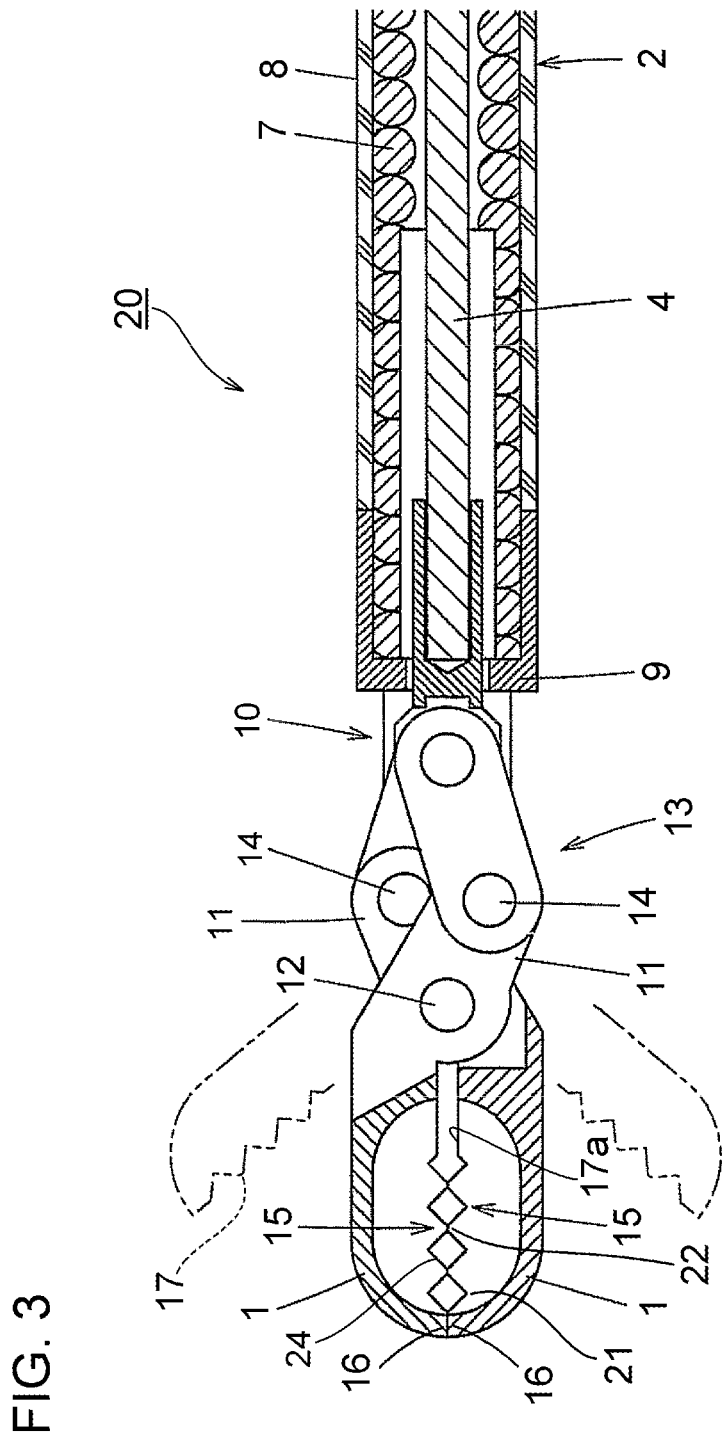
FIG. 3 is a lateral cross-sectional view of the distal portion of the endoscopic high-frequency hemostatic forceps according to the first embodiment of the present invention.

FIG. 3 is a lateral cross-sectional view of a distal portion of hemostatic forceps 20. As shown therein, the flexible sheath 2 is formed of a close-wound coil 7 coated with an electrically insulative flexible tube 8. A support frame 9 attached to the distal portion of the flexible sheath 2 is split by a slit 10 having an open front end, as most of the known endoscopic forceps. Drive arms 11 formed integrally with the respective forceps cups 1 so as to backwardly extend therefrom are loosely located in the slit 10, and a pivotal shaft 12 provided across the slit 10 serves to pivotally support a front end portion of the drive arms 11. Accordingly, the pair of forceps cups 1 are able to freely change into a state where front portions of the pair of forceps cups 1 are open, or a state where the pair of forceps cups 1 are close like a crocodile mouth, about the pivotal shaft 12.

A known link mechanism 13 that converts a sliding motion of the operating wire 4 into a rotational motion of the drive arm 11 about the pivotal shaft 12 is provided in the slit 10 of the support frame 9. A joint shaft 14 pivotally connects the drive arms 11 and the link mechanism 13. Thus, upon operating the slider 5 at the manipulating portion 3 so as to longitudinally slide the operating wire 4, the drive arms 11 are caused to rotate about the pivotal shaft 12 by the link mechanism 13, so that the pair of forceps cups 1 opens and closes in a forward direction about the pivotal shaft 12.

The forceps cup 1 includes a closing-side surface 17 on the side thereof opposing the mating forceps cup 1. When the pair of forceps cups 1 opens and closes, the respective closing-side surfaces 17 come closer to and move away from each other.

In the hemostatic forceps 20 according to this embodiment, the closing-side surface 17 includes a front edge portion 16, a sawtooth portion 15 and a planar portion 17a (FIG. 1).

FIG. 1 depicts the forceps cups 1 in an opened state. FIG. 3 depicts the forceps cups 1 in a closed state by solid lines, indicating the opened state by dash-dot-dot lines.

Although the forceps cup 1 is caused to rotate in a hinge form about the pivotal shaft 12 according to this embodiment, the present invention is not limited to such a configuration. For example, the pair of forceps cups 1 may come closer to and move away from each other keeping the respective closing-side surfaces 17 parallel to each other.

The pair of forceps cups 1 serving as a high-frequency electrode and the drive arm 11 integrally formed therewith are constituted of a conductive metal. The forceps cups 1 each have a cup shape having an opening 23 (FIG. 1) formed on the closing-side surface 17. The opening 23 defines a recess formed generally in a central portion of the closing-side surface 17.

As shown in FIGS. 1 and 3, the openings 23 of the pair of forceps cups 1 are accurately aligned with each other when the forceps cups 1 are completely closed. A sawtooth portion 15 having a plurality (for example, 2 to 5) of concavo-convex structures which constitute a sawtooth-shape is provided on the respective side edge portions 19 in an outer periphery 18 of the closing-side surface 17 of each forceps cup 1.

The sawtooth portion 15 is not provided on a front edge portion 16 of the closing-side surface 17. In the hemostatic forceps 20 intended for hemostasis of an entire biological tissue without resection a part thereof according to this embodiment, forming the front edge portion 16 in a planar shape without providing thereon the sawtooth portion 15 prevents a base portion of the biological tissue from being subjected to concentration of an excessive pressure, thereby preventing a perforation in the biological tissue.

As shown in FIG. 3, the pair of forceps cups (forceps elements) 1 is each provided with the sawtooth portion 15 on the respective closing-side surface 17, in the hemostatic forceps 20 according to this embodiment. When the pair of forceps cups 1 is closed, the top portions 22 of the sawtooth portions 15 of each of the pair of forceps cups 1 confront each other.

When pair of forceps cups 1 is closed, the top portion 22 of the sawtooth portion 15 of one of the forceps cups 1 and that of the sawtooth portion 15 of the other forceps cup 1 may be brought into contact with each other or remain spaced with a predetermined clearance therebetween.

The top portions 22 of the sawtooth portion 15 may project upward with respect to the closing-side surface 17 as shown in FIG. 3, or be flush with the closing-side surface 17 or be recessed downward with respect thereto. However, forming the top portions 22 of the sawtooth portion 15 so as to project upward with respect to the closing-side surface 17 as in this embodiment keeps the opposing planar portions 17a from contacting each other when the forceps cups 1 are closed as shown in FIG. 3. Accordingly, a part of the biological tissue can protrude through the gaps between the opposing planar portions 17a, which facilitates the pair of forceps cups 1 to be properly closed.

The forceps cup 1 according to this embodiment is provided with an electrically insulative coating such as a fluorine resin coating, over an entirety of the inner and outer surface, except for the outer periphery 18 of the closing-side surface 17. The drive arms 11 may be or may not be provided with the electrically insulative coating, however at least the inner circumferential surface of the shaft hole through which the joint shaft 14 is located constitutes an exposed metal surface, so that a high-frequency current supplied through the operating wire 4 is led to the forceps cup 1 through the joint shaft 14. The pair of drive arms 11 is monopolar high-frequency electrodes electrically connected to each other.

The sawtooth portion 15 includes a plurality of projections formed with a spacing between each other. The shape of the projection is not specifically limited, and for example the top portion 22 of the sawtooth-shape of the sawtooth portion 15 includes a planar surface in the forceps cup 1 according to this embodiment. Between the top portions 22 a V-shaped bottom portion 21 is provided. A lateral portion 24 between the top portions 22 and the bottom portion 21 constitutes a sloped surface.

The sawtooth portion 15 is provided with the electrically insulative coating except for the top portions 22. Here, the "planar surface" of the top portion 22 of the sawtooth portion 15 refers to the case where the top portion 22 includes a slightly sloped portion of a milder inclination angle than the lateral portion 24, a recessed portion, or a protruding portion, in addition to the case where the top portion 22 is a flat plane parallel to the planar portion 17a of the closing-side surface 17.

In this embodiment, the sawtooth portions 15 of the pair of forceps cups 1 each include an exposed metal surface 15a where the conductive metal is exposed, only in the top portions 22 of each projecting shape. Accordingly, the top portions 22 are conductive.

In other words, the sawtooth portion 15 is provided with the electrically insulative coating except for the top portions 22, i.e., on the bottom portions 21 and the lateral portions 24.

In the forceps cup 1 according to this embodiment, the front edge portion 16 of the closing-side surface 17 is not provided with the electrically insulative coating, and is hence conductive.

More specifically, the conductive metal is exposed in the front edge portion 16. In FIG. 1, hatched portions indicate the exposed metal surface 15a of the sawtooth portion 15 and the exposed metal surface 16a of the front edge portion 16, which are conductive.

Here, the exposed metal surface 15a and the exposed metal surface 16a may be plated with a metal different from the conductive metal constituting the forceps cup 1, thus to be made conductive.

In the case where a biological tissue is pinched by the hemostatic forceps 20 according to this embodiment, in which the forceps cups 1 rotate in a hinge form, the front edge portion 16 applies a heavy pressure to the biological tissue. Accordingly, forming the front edge portion 16 in a planar shape without the sawtooth portion 15 as in this embodiment can prevent the biological tissue from suffering a perforation, thus enabling the part for hemostasis to be safely protected.

Likewise, forming the top portion 22 of the sawtooth-shape of the sawtooth portion 15 in a planar shape prevents the part for hemostasis pinched by the forceps cups 1 from suffering a perforation.

Figure 4:
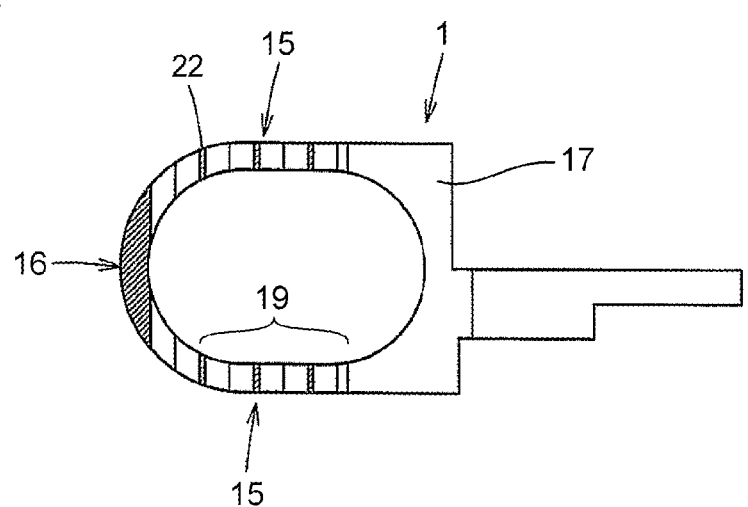
FIG. 4 is a front view of a closing-side surface of a forceps cup according to the first embodiment of the present invention.

FIG. 4 illustrates a single piece of the forceps cup 1 viewed in a direction perpendicular to the closing-side surface 17. In the forceps cup 1 according to this embodiment, the top portions 22 of the sawtooth portion 15 form a strip shape extending in a widthwise direction of the forceps cup 1 (vertical direction in FIG. 4), and the adjacent top portions 22 are parallel to each other. For clearer understanding, the top portions 22 of the sawtooth portion 15 and the front edge portion 16 are hatched in FIG. 4.

Forming the exposed metal surface of the front edge portion 16 in a large size leads to degraded hemostatic effect, in which case the front edge portion 16 of the closing-side surface 17 may be provided with the electrically insulative coating. The electrically insulative coating may be provided in a part or whole of the front edge portion 16. Since an optimum hemostatic effect can be attained by forming the exposed metal surface in an appropriate size, the size of the exposed surface of the front edge portion 16 may be adjusted as desired.

In the hemostatic forceps 20 according to this embodiment, the pair of forceps cups (forceps elements) 1 each includes the sawtooth portion 15 formed on the respective closing-side surfaces 17. The pair of forceps cups 1 is monopolar high-frequency electrodes electrically connected to each other.

When a biological tissue is pinched between the pair of forceps cups 1 of the hemostatic forceps 20 thus configured, the exposed metal surface 15a to be brought into contact with the biological tissue is limited to the top portions 22 of the sawtooth portions 15 which have a quite small area, with respect to the side edge portion 19 of the closing-side surface 17 of the forceps cup 1.

Figure 5:
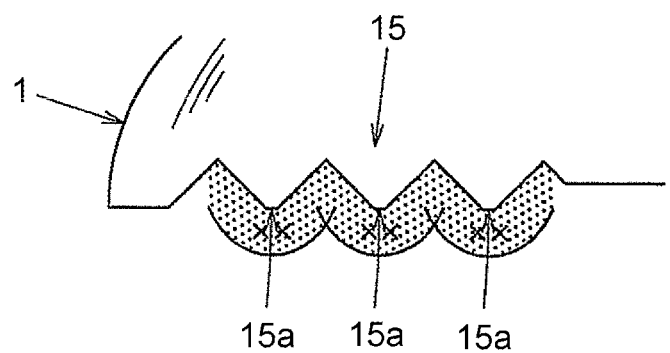
FIG. 5 is a schematic drawing for explaining a hemostatic treatment process performed by the endoscopic high-frequency hemostatic forceps according to the first embodiment of the present invention.

FIG. 5 schematically illustrates the sawtooth portion 15 of the forceps cup 1 and the biological tissue thereby pinched.

As shown therein, upon supplying a high-frequency current to the pair of forceps cups 1 pinching the biological tissue therebetween, a portion of the biological tissue in contact with the exposed metal surface 15a is quickly heated and coagulated by cauterization, and thus the hemostatic effect can be rapidly attained. Therefore, the biological tissue can be exempted from tissue destruction due to a deep burn. In addition, when the coagulated region of the biological tissue spreads to a portion thereof located in the gaps between the lateral portions 24 of the sawtooth portion 15, the adjacent coagulated regions overlap thereby improving the hemostatic efficiency, which allows the hemostatic treatment to be completed in an extremely short time and with a low current value.

Figure 6:
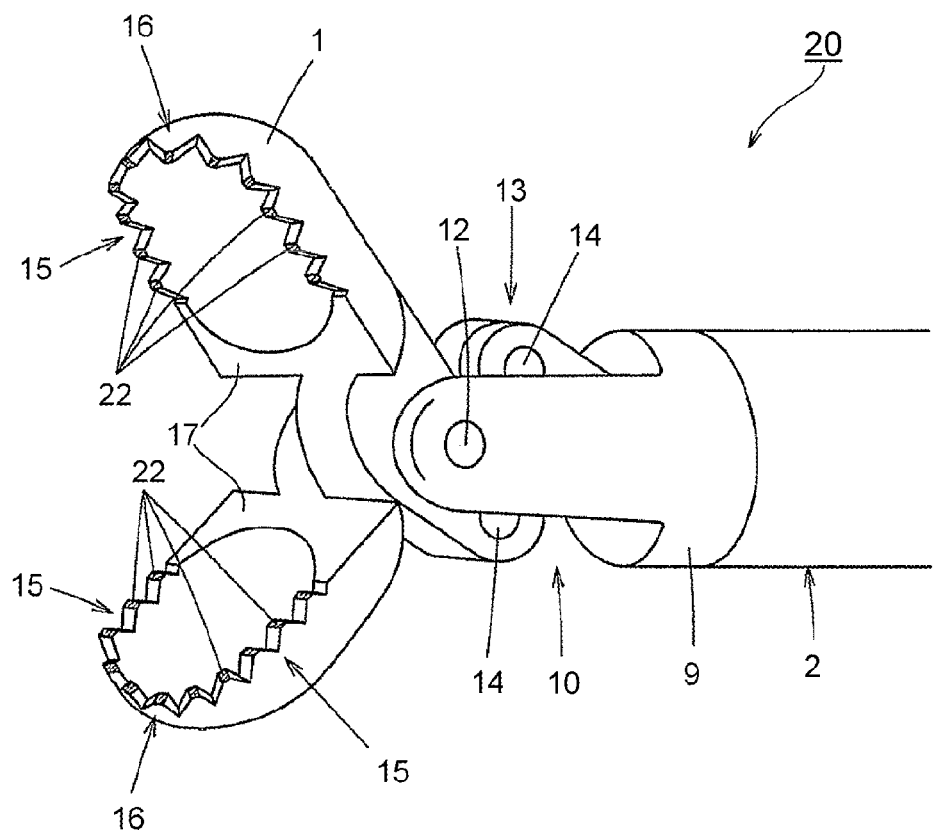
FIG. 6 is a perspective view showing a distal portion of an endoscopic high-frequency hemostatic forceps according to a second embodiment of the present invention.

FIG. 6 shows a distal portion of the hemostatic forceps 20 according to a second embodiment of the present invention. In this embodiment, the sawtooth portion 15 are provided on the front edge portion 16 of the outer periphery 18 of the respective closing-side surfaces 17 of the pair of forceps cups 1, in addition to the side edge portions 19.

Each of the sawtooth portion 15 is provided with the electrically insulative coating over its entirety except for the respective top portions 22, and hence the exposed metal surface 15a where the conductive metal is exposed is formed only in the top portions 22 of the sawtooth portion 15. The configuration of the remaining portion is the same as that of the first embodiment. Forming thus the sawtooth portion 15 on the front edge portion 16 and the respective side edge portions 19 of the closing-side surface 17 of the forceps cup 1 leaving only the top portions 22 as the exposed metal surface 15a enables the hemostatic treatment to be performed even more quickly.

Figure 7:
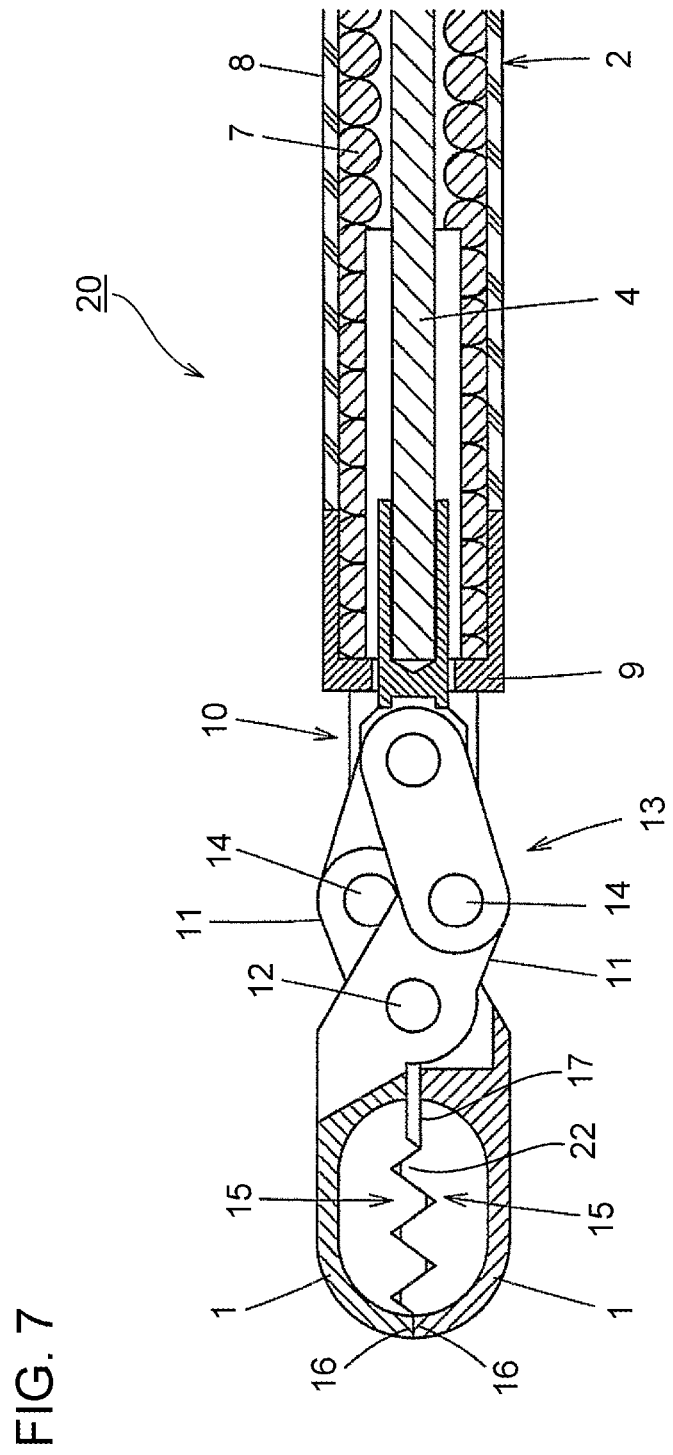
FIG. 7 is a lateral cross-sectional view of a distal portion of an endoscopic high-frequency hemostatic forceps according to a third embodiment of the present invention.

FIG. 7 shows a distal portion of the hemostatic forceps 20 according to a third embodiment of the present invention. In this embodiment, the pair of forceps cups (forceps elements) 1 each includes the sawtooth portion 15 on the closing-side surface 17, and the respective sawtooth portions 15 of each of the pair of forceps cups 1 are engaged with each other when the forceps cups 1 are closed. In other words, the hemostatic forceps 20 according to this embodiment is different from the first embodiment (see FIG. 3) in that the sawtooth portions 15 of the upper and lower forceps cup 1 are alternately located.

As in the first embodiment, the sawtooth portion 15 is not provided on the front edge portion 16 of the closing-side surface 17 of the pair of forceps cups 1, and the front edge portion 16 is provided with the electrically insulative coating. Accordingly, the conductive metal constituting the forceps cup 1 is exposed only in the top portions 22 of the sawtooth portion 15 formed on the side edge portions 19 (see FIG. 6). The configuration of the remaining portion is the same as that of the first embodiment.

Figure 8:
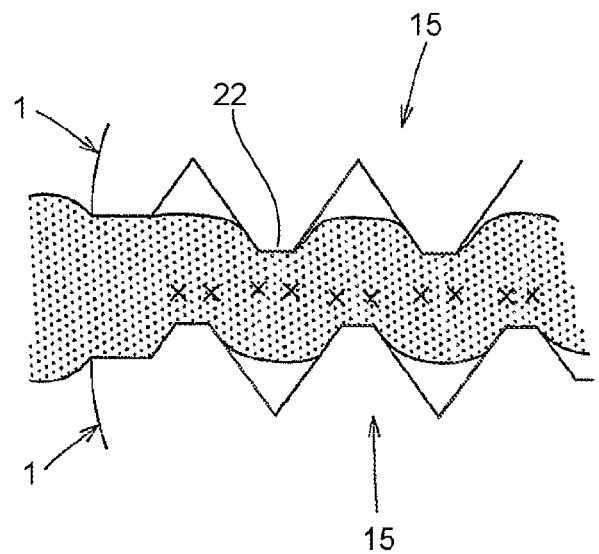
FIG. 8 is a schematic drawing for explaining a hemostatic treatment process performed by the endoscopic high-frequency hemostatic forceps according to the third embodiment of the present invention.

Upon supplying a high-frequency current to the pair of forceps cups 1 thus configured according to the third embodiment, with a biological tissue pinched therebetween, the hemostatic treatment can be completed in a still shorter time and with a still lower output than in the first embodiment, as schematically illustrated in FIG. 8. This is not only because the exposed metal surface 15a is provided only on the top portions 22 of the sawtooth portions 15 and hence has a quite small area, but because the exposed metal surfaces 15a of the pair of forceps cups 1 are alternately located and therefore the pitch between the exposed metal surfaces 15a is narrower. Further, since the front edge portion 16 is provided with the electrically insulative coating, a portion of the biological tissue in contact with the front edge portion 16 is kept from being cauterized and coagulated, and a muscular layer can be exempted from being burnt and suffering a perforation. Here, as a variation of the third embodiment, the sawtooth portion 15 may also be provided on the respective front edge portions 16 of the pair of forceps cups 1, with the exposed metal surface 15a formed in the top portions 22 of the sawtooth portion 15, as in the second embodiment (see FIG. 6).

Figure 9:
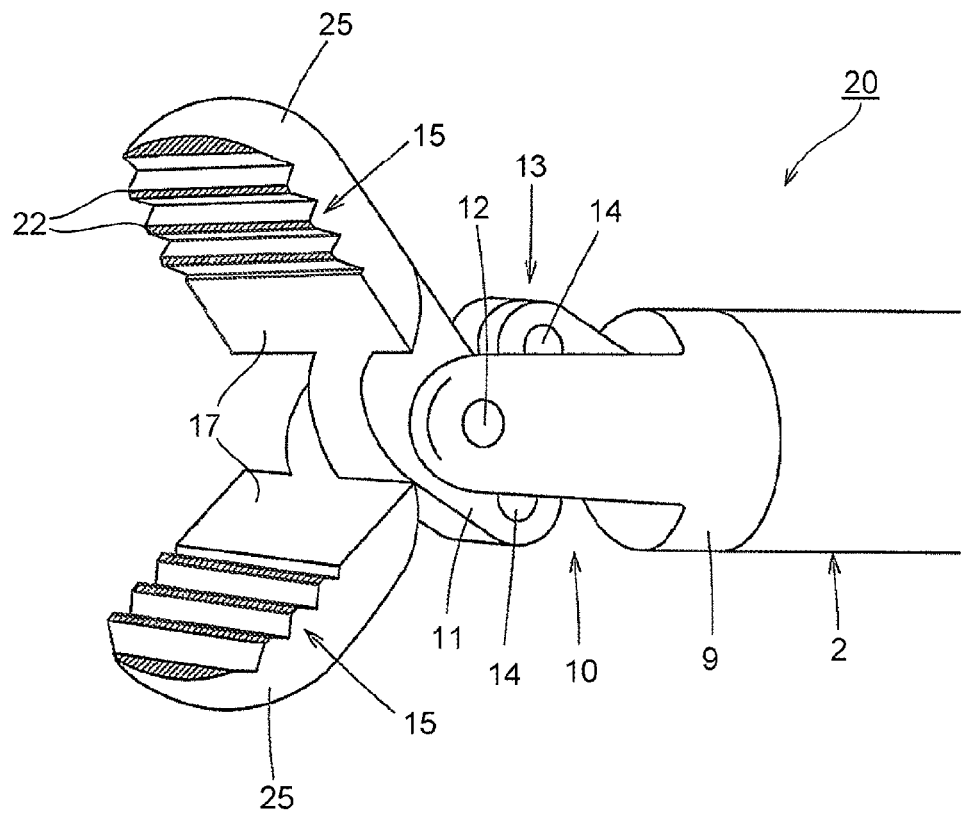
FIG. 9 is a perspective view showing a distal portion of an endoscopic high-frequency hemostatic forceps according to a fourth embodiment of the present invention.

FIG. 9 shows a distal portion of the hemostatic forceps 20 according to a fourth embodiment of the present invention. In this embodiment, a pair of forceps elements (high-frequency electrodes) 25 of a block shape is provided instead of the hollow forceps caps 1 according to the first to the third embodiments. The top portions 22 according to this embodiment is formed in a strip shape continuously extending from one end to the other of the forceps element 25 in a widthwise direction thereof.

The forceps element 25 includes the sawtooth portion 15 on the closing-side surface 17, and only the top portions 22 of the sawtooth portion 15 constitutes the exposed metal surface 15a. A sawtooth portion having a plurality of strip-shaped concavo-convex structures which constitute a sawtooth-shape is provided on the forceps element 25. The plurality of strip-shaped concavo-convex structures are aligned in a front-to-back direction of the hemostatic forceps 20 from a distal portion toward a proximal portion thereof. Also, the closing-side surface 17 includes a region where the sawtooth portion 15 is not provided, in a part of the proximal region of the forceps element 25.

In the forceps element 25 according to this embodiment also, the conductive top portion 22 is provided on a front edge portion thereof.

Such a configuration also allows a hemostatic treatment for an extensive slightly bleeding part to be performed without causing a deep burn in the biological tissue, thereby attaining a desired hemostatic effect. In particular, the hemostatic forceps 20 according to this embodiment can retain a biological tissue in a sheet form by the plurality of strip-shaped top portions 22, so as to perform the hemostatic treatment of a relatively large bleeding part.

Figure 10:
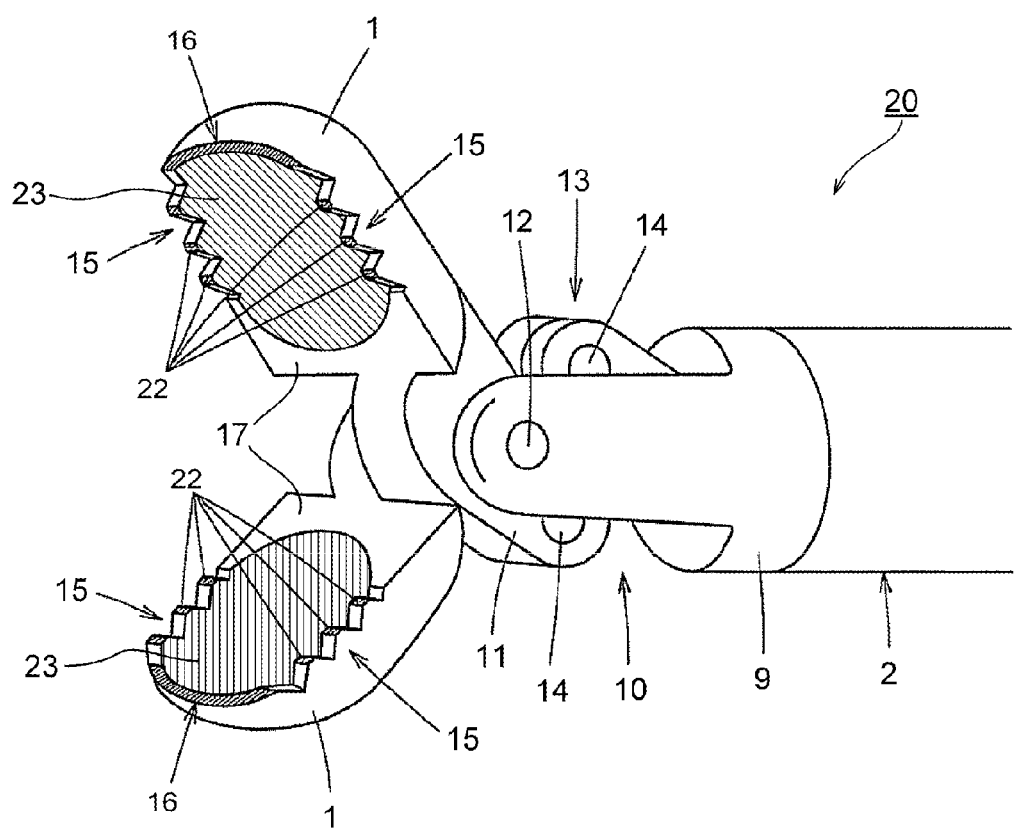
FIG. 10 is a perspective view showing a distal portion of an endoscopic high-frequency hemostatic forceps according to a fifth embodiment of the present invention.
Figure 11:
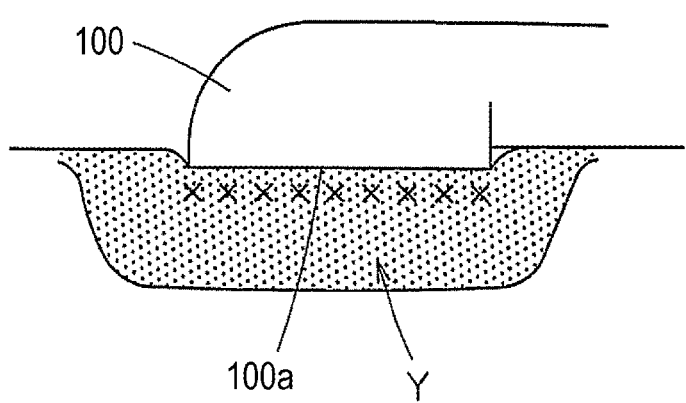
FIG. 11 is a schematic drawing for explaining a hemostatic treatment process performed by a conventional high-frequency treatment instrument.

FIG. 10 is a perspective view showing a distal portion of the hemostatic forceps 20 according to a fifth embodiment of the present invention.

In the hemostatic forceps 20 according to this embodiment, the pair of forceps cups (forceps elements) 1 each includes the opening 23 on the respective closing-side surface 17, as in the first embodiment. However, a difference from the first embodiment lies in that the inner surface of the opening 23 is not provided with the electrically insulative coating, and is hence conductive.

In this embodiment, the conductive metal constituting the forceps cup 1 is exposed in the top portions 22 (exposed metal surfaces 15a) of the sawtooth portion 15, the exposed metal surface 16a of the front edge portion 16, and in the inner surface of the opening 23. Such a configuration allows a high-frequency current to be supplied also to a portion of the biological tissue in contact with the inner surface of the opening 23. Therefore, the configuration according to this embodiment allows the high-frequency current to be supplied to an entirety of the biological tissue, while limiting the power supply area to the top portions 22 of the sawtooth portions 15. Consequently, an excellent hemostatic effect can be attained without causing a deep burn in the biological tissue.

The configuration according to this embodiment allows the power supply area to be limited to the top portions 22 in the sawtooth portions 15, and yet allows the current to be supplied to the entirety of the biological tissue through the inner surface of the opening 23. Therefore, an excellent hemostatic effect can be attained without causing a deep burn in the biological tissue. Employing the hemostatic forceps 20 thus configured according to this embodiment for a projecting biological tissue such as a polyp bleeding from an entire portion thereof from its proximal portion to its distal portion provides the following advantages. According to this embodiment, the proximal portion of the biological tissue can be quickly subjected to the hemostatic treatment with the top portions 22 of the sawtooth portions 15 and the exposed metal surface 16a of the front edge portion 16 so that blood supply to the biological tissue is blocked, and the cup-shaped inner surface of the opening 23 can coagulate the entire distal portion of the biological tissue by cauterization. Thus, the hemostatic treatment can be safely and quickly performed for an entirety of a projecting biological tissue without causing a deep burn in the biological tissue.

In other words, making the inner surface of the opening 23 of the forceps cup 1 conductive allows the high-frequency current to be supplied to an entirety of the biological tissue through the inner surface of the opening 23, while limiting the power supply area to the top portions 22 of the sawtooth portions 15. Thus the configuration according to this embodiment enables an excellent hemostatic effect to be attained without causing a deep burn in the biological tissue.

As stated above, the conductive metal is exposed over the entire inner surface of the opening 23 in the hemostatic forceps 20 according to this embodiment. Alternatively, however, the conductive metal may be partially exposed in the inner surface of the opening 23, to adjust the hemostatic effect with respect to the biological tissue.

Although the pair of forceps cups 1 are electrically connected to each other and serves as monopolar electrodes in the foregoing embodiments of the present invention, the present invention may be applied to a bipolar high-frequency hemostatic forceps in which the pair of forceps cups 1 is electrically insulated from each other and an anode and a cathode of the high-frequency power source are independently connected.

In addition, the same material or different materials may be employed for the electrically insulative coating to be provided on the outer surface of the forceps cup 1, the planar portion 17a of the closing-side surface 17, and the lateral portion 24 of the sawtooth portion 15.

This application claims priority based on Japanese Patent Application No. 2009-116192 filed on May 13, 2009, the entire content of which is incorporated hereinto.

The invention claimed is:

1. An endoscopic high-frequency hemostatic forceps including a pair of forceps elements constituted of a conductive metal so as to serve as a high-frequency electrode, and configured to be able to freely change into a state where front portions of the pair of forceps elements are open, or a state where the pair of forceps elements are closed, the hemostatic forceps comprising:

a sawtooth portion having a plurality of concavo-convex structures which constitute a sawtooth-shape formed on at least one of the respective opposing closing-side surfaces of the pair of forceps elements, wherein a bottom portion of the sawtooth-shape of the sawtooth portion is provided with an electrically insulative coating, and a top portion of the sawtooth-shape of the sawtooth portion is not provided with the electrically insulative coating, wherein the sawtooth portion is not provided on a front edge portions of the closing-side surfaces of the pair of forceps elements, wherein the front edge portions of the closing-side surfaces of the pair of forceps elements are not provided with the electrically insulative coating and are conductive; and wherein the top portion of the sawtooth-shape of the sawtooth portion is formed in a flat shape, the sawtooth portion is provided with the electrically insulative coating except for the top portion and a top flat surface of the saw tooth-shape is conductive, but a side surface of the saw tooth-shape is insulated.

2. The endoscopic high-frequency hemostatic forceps according to claim 1, wherein the pair of forceps elements each includes the sawtooth portion formed on the respective closing-side surfaces, such that top portions of the respective sawtooth portions of the pair of forceps elements confront each other when the pair of forceps elements are closed.

3. The endoscopic high-frequency hemostatic forceps according to claim 1, wherein the pair of forceps elements each includes the sawtooth portion formed on the respective closing-side surfaces, such that the respective sawtooth portions of the pair of forceps elements are engaged with each other when the pair of forceps elements are closed.

4. The endoscopic high-frequency hemostatic forceps according to claim 1, wherein the pair of forceps elements each includes an opening formed on the respective closing-side surfaces, and an inner surface of the opening is not provided with the electrically insulative coating, and is conductive.

5. The endoscopic high-frequency hemostatic forceps according to claim 1, wherein the pair of forceps elements each includes the sawtooth portion formed on the respective closing-side surfaces, and the pair of forceps elements electrically connected to each other and serves as a monopolar high-frequency electrode.

6. The endoscopic high-frequency hemostatic forceps according to claim 1, wherein the front edge portion of the closing-side surface of each of the pair of forceps elements is free of the sawtooth portion, wherein the front edge portion of the closing-side surface of each of the pair of forceps elements are flattened, wherein the front edge portion of the closing-side surface of each of the pair of forceps elements face each other when the pair of forceps elements are closed.

* * * * *